United States Patent
Flückiger et al.

[11] Patent Number: 5,646,145
[45] Date of Patent: Jul. 8, 1997

[54] METHOD OF CONTROLLING INSECTS

[75] Inventors: Claude Flückiger, Magden; Alfred Rindlisbacher, Muttenz; Robert Senn, Basel; Solang Uk, Rheinfelden, all of Switzerland

[73] Assignee: Ciba-Geigy Corporation, Tarrytown, N.Y.

[21] Appl. No.: 453,934

[22] Filed: May 30, 1995

Related U.S. Application Data

[63] Continuation of Ser. No. 342,687, Nov. 21, 1994, abandoned, which is a continuation of Ser. No. 111,343, Aug. 24, 1993, abandoned.

[30] Foreign Application Priority Data

Sep. 10, 1992 [CH] Switzerland ............... 2847/92
Nov. 20, 1992 [CH] Switzerland ............... 3558/92

[51] Int. Cl.$^6$ ................................ A01N 43/64
[52] U.S. Cl. ........................................ 514/242
[58] Field of Search ................................ 514/242

[56] References Cited

U.S. PATENT DOCUMENTS

| | | | |
|---|---|---|---|
| 4,931,439 | 6/1990 | Kristinsson | 514/242 |
| 5,179,094 | 1/1993 | Kristiansen et al. | 514/242 |

*Primary Examiner*—Allen J. Robinson
*Attorney, Agent, or Firm*—William A. Teoli, Jr.; Marla J. Mathias

[57] ABSTRACT

The invention relates to a method of controlling insects in which compounds of the formula

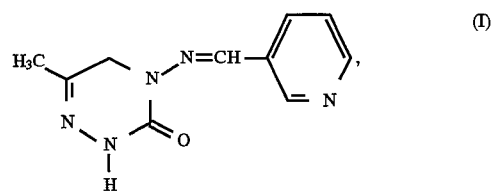

(I)

in free form or in agrochemically acceptable salt form, are used, wherein specific insects of the order Homoptera are controlled, to the corresponding use of those compounds, to corresponding insecticidal compositions, the active ingredient of which is selected from those compounds, and to a process for the preparation of and to the use of those compositions. The invention relates also to a method of protecting plant propagation material against attack by pests, wherein compounds of formula I, in free form or in agrochemically acceptable salt form, are used, to the corresponding use of those compounds, to corresponding pesticidal compositions, the active ingredient of which is selected from those compounds, to a process for the preparation of and to the use of those compositions, and to plant propagation material correspondingly protected against attack by pests.

10 Claims, No Drawings

METHOD OF CONTROLLING INSECTS

This application is a continuation of application Ser. No. 08/342,687 filed Nov. 21, 1994, now abandoned, which is a continuation of application Ser. No. 08/111,343 filed Aug. 24, 1993, now abandoned.

The invention relates (A) to a method of controlling insects, wherein compounds of the formula

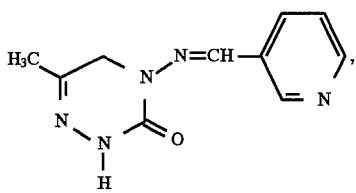

(I)

in free form or in agrochemically acceptable salt form, are used, wherein specific insects of the order Homoptera are controlled, to the corresponding use of those compounds, to corresponding insecticidal compositions, the active ingredient of which is selected from those compounds, and to a process for the preparation of and to the use of those compositions. One, several or all of the subjects according to the invention from this paragraph are, where appropriate, referred to hereinafter under the label "area (A) of the subject of the invention" or under the label "(A)".

The invention relates (B) to a method of protecting plant propagation material from attack by pests, wherein compounds of the formula

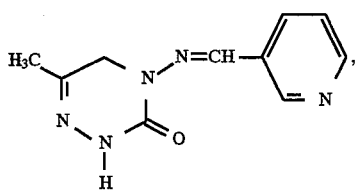

(I)

in free form or in agrochemically acceptable salt form, are used, to the corresponding use of those compounds, to corresponding pesticidal compositions, the active ingredient of which is selected from those compounds, to a process for the preparation of and to the use of those compositions, and to plant propagation material correspondingly protected against attack by pests. One, several or all of the subjects according to the invention from this paragraph are, where appropriate, referred to hereinafter under the label "area (B) of the subject of the invention" or under the label "(B)".

Agrochemically acceptable salts of the compounds I are, for example, acid addition salts. Those salts are formed, for example, with strong inorganic acids, such as mineral acids, for example perchloric acid, sulfuric acid, nitric acid, nitrous acid, a phosphoric acid or a hydrohalic acid, with strong organic carboxylic acids, such as unsubstituted or substituted, for example halogen-substituted, $C_1$–$C_4$alkanecarboxylic acids, for example formic acid, acetic acid or trifluoroacetic acid, unsaturated or saturated dicarboxylic acids, for example oxalic, malonic, succinic, maleic, fumaric or phthalic acid, hydroxycarboxylic acids, for example ascorbic, lactic, malic, tartaric or citric acid, or benzoic acid, or with organic sulfonic acids, such as unsubstituted or substituted, for example halogen-substituted, $C_1$–$C_4$alkane- or aryl-sulfonic acids, for example methane- or p-toluene-sulfonic acid. In view of the close relationship between the compounds I in free form and in the form of their agrochemically acceptable salts, hereinbefore and hereinafter any reference to the free compounds I or their agrochemically acceptable salts is to be understood as including also the corresponding agrochemically acceptable salts or the free compounds I, respectively, where appropriate and expedient. According to the invention the free form of the compounds I is preferred.

The compounds I, in free form or in agrochemically acceptable salt form, are in the form of (E) or (Z) isomers, depending on whether the (—N═C(H)—) partial structure, which links the two heterocycles shown in the structural formula disclosed above, has the (E) or the (Z) configuration. Accordingly, hereinbefore and hereinafter the compounds I, in free form or in agrochemically acceptable salt form, are to be understood as being the corresponding (E) or (Z) isomers, in each case in pure form or in the form of (E)/(Z) mixtures, even if not specifically mentioned in every case.

The compounds I, in free form or in agrochemically acceptable salt form, may be in the form of tautomers. For example, a compound I which, according to the structural formula disclosed above, has a (—N(H)—C(═O)—) partial structure may be in equilibrium with the tautomer that has a (—N═C(OH)—) partial structure instead of the (—N(H)—C(═O)—) partial structure. Accordingly, hereinbefore and hereinafter any reference to the compounds I, in free form or in agrochemically acceptable salt form, is also, where appropriate, to be understood as including corresponding tautomers, even when the latter are not specifically mentioned in every case.

The compounds I used according to the invention are known and are described, for example, in EP-A-0 314 615. EP-A-0 314 615 gives a general description of the activity of compounds of the formula

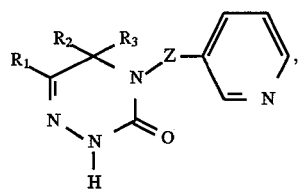

(II)

wherein either $R_1$ is hydrogen, $C_1$–$C_{12}$alkyl, $C_3$–$C_6$cycloalkyl, $C_1$–$C_4$alkoxy-$C_1$–$C_6$alkyl, halo-$C_1$–$C_2$alkyl, phenyl, benzyl, phenethyl, phenylpropyl, phenylbutyl or phenylpentyl, or a phenyl, benzyl, phenethyl, phenylpropyl, phenylbutyl or phenylpentyl radical mono- or all-substituted by halogen, $C_1$–$C_5$alkyl, halo-$C_1$–$C_2$alkyl, methoxy and/or by ethoxy, and $R_2$ is hydrogen, $C_1$–$C_6$alkyl or $C_3$–$C_6$cycloalkyl, or phenyl that is unsubstituted or substituted by $C_1$–$C_{12}$alkyl, halogen or by halo-$C_1$–$C_{12}$alkyl, or $R_1$ and $R_2$ together form a saturated or unsaturated 3- to 7-membered carbocycle, $R_3$ is hydrogen or $C_1$–$C_6$alkyl, and Z is —N═CH— or —NH—CH$_2$—, in free form or in acid addition salt form, in the control of pests, especially insects, more especially insects of the orders Anoplura, Coleoptera, Diptera, Heteroptera, Homoptera, Hymenoptera, Isoptera, Lepidoptera, Mallophaga, Orthoptera, Psocoptera, Siphonaptera, Thysanoptera and Thysanura, especially sucking insects, more especially insects of the Aphididae family, which belongs to the order Homoptera. However, EP-A-0 314 615 specifically discloses the activity of the compounds II against only three species of the order Homoptera, namely the species *Aphis craccivora*, *Aphis fabae* and *Myzus persicae*, which come from the Aphididae family and which belong to the genera Aphis and Myzus, and against one species of the order Diptera, namely the species *Aedes aegypti* which comes from the Culicidae family and which belongs to the genus Aedes. However, apart from the Aphididae family, no other families from the order Homoptera are proposed as target insects, and likewise no genera of the Aphididae family nor, apart from the species *Aphis craccivora* and *Aphis fabae*, any other species of the genus Aphis. Finally, there is also no disclosure whatever in EP-A-0 314 615 regarding the use of compounds II in the protection of plant propagation material against attack by pests.

Unexpectedly and, in view of the disclosure discussed above of EP-A-0 314 615, entirely surprisingly, it has now been found that (A) the compounds I are excellently suitable for the control of certain other insects of the order Homoptera, namely for the control of insects of the families Aleyrodidae, Cicadellidae and Delphacidae, which belong to the order Homoptera, of insects of the genera Acyrthosiphon, Brachycaudus, Brevicoryne, Dysaphis, Hyalopterus, Macrosiphum, Phorodon, Rhopalosiphum, Sappaphis, Schizaphis and Toxoptera from the Aphididae family, which belongs to the order Homoptera, and of insects of the species *Aphis gossypii* and *Aphis pomi*, which belong to the genus Aphis and come from the Aphididae family, which belongs to the order Homoptera, and that (B) the compounds I are also excellently suitable for the protection of plant propagation material against attack by pests.

This excellent suitability of the compounds I for the control of specific insects of the order Homoptera according to (A) and for the protection of plant propagation material against attack by pests according to (B) is so surprising because, although the compounds I fall within the scope of the compounds of formula II disclosed by EP-A-0 314 615 and are even specifically disclosed in Example H.3 of EP-A-0 314 615, EP-A-0 314 615 makes no mention whatever of the excellent activity or suitability according to the present invention, neither of an especially pronounced activity of the compounds II against the specific insects mentioned according to the invention of the order Homoptera according to (A), nor of an especially pronounced suitability of the compounds II for the protection according to the invention of plant propagation material against attack by pests according to (B), let alone of a corresponding especially pronounced activity or suitability of the present compounds I, which may be regarded as a special sub-group of the compounds II.

The control of insects according to (A) and the protection of plant propagation material against attack by pests according to (B) are of great importance for the user in the field of insect and pest control because, without the targeted control of those insects and pests, for example, great economic losses are suffered, for example as a result of the damage they cause to agricultural products.

Within the scope of area (A) of the subject of the invention, it is possible to control especially (1) insects of the Aleyrodidae family, especially of the genera Bemisia and Trialeurodes;

(2) insects of the Cicadellidae family, especially of the genera Empoasca and Erythroneura;

(3) insects of the Delphacidae family, especially of the genera Laodelphax and Nilaparvata, more especially of the species *Laodelphax striatellus* and *Nilaparvata lugens*;

(4) insects of the genera Acyrthosiphon, Brachycaudus, Brevicoryne, Dysaphis, Hyalopterus, Macrosiphum, Phorodon, Rhopalosiphum, Sappaphis, Schizaphis and Toxoptera from the Aphididae family, especially of the genera Acyrthosiphon, Brevicoryne, Hyalopterus, Macrosiphum, Phorodon, Sappaphis, Schizaphis and Toxoptera, preferably of the genera Brevicoryne, Hyalopterus, Macrosiphum, Phorodon and Toxoptera, more especially of the species *Brevicoryne brassicae*, *Hyalopterus amygdali*, *Macrosiphum euphorbiae*, *Phorodon humuli*, *Toxoptera aurantii* and *Toxoptera citricida*;

(5) insects of the species *Aphis gossypii* and *Aphis pomi* from the genus Aphis from the Aphididae family; or (6) insects selected from the group of species of insects consisting of (a) *Acyrthosiphon pisum*; (b) *Aphis gossypii*; (c) *Aphis pomi*; (d) *Bemisia tabaci*; (e) *Brachycaudus persicaecola*; (f) *Brevicoryne brassicae*; (g) *Dysaphis devecta*; (h) *Dysaphis plantaginea*; (i) *Empoasca flavescens*; (j) *Erythroneura apicalis*; (k) *Hyalopterus amygdali*; (l) *Laodelphax striatellus*; (m) *Macrosiphum avenae*; (n) *Macrosiphum euphorbiae*; (o) *Macrosiphum rosae*; (p) *Nilaparvata lugens*; (q) *Phorodon humuli*; (r) *Rhopalosiphum insertum*; (s) *Rhopalosiphum padi*; (t) *Rhopalosiphum pseudobrassicae*; (u) *Sappaphis piricola*; (v) *Schizaphis graminum*; (w) *Toxoptera aurantii*; (x) *Toxoptera citricida*; and (y) *Trialeurodes vaporariorum*.

Within the scope of area (B) of the subject of the invention it is possible to control especially (7) animal pests;

(8) insects and representatives of the order Acarina;

(9) insects of the order Lepidoptera, for example *Acleris spp.*, *Adoxophyes spp.*, *Aegeria spp.*, *Agrotis spp.*, *Alabama argillaceae*, *Amylois spp.*, *Anticarsia gemmatalis*, *Archips spp.*, *Argyrotaenia spp.*, *Autographa spp.*, *Busscola fusca*, *Cadra cautella*, *Carposina nipponensis*, *Chilo spp.*, *Choristoneura spp.*, *Clysia ambiguella*, *Cnaphalocrocis spp.*, *Cnephasia spp.*, *Cochylis spp.*, *Coleophora spp.*, *Crocidolomia binotalis*, *Cryptophlebia leucotreta*, *Cydia spp.*, *Diatraea spp.*, *Diparopsis castanea*, *Earias spp.*, *Ephestia spp.*, *Eucosma spp.*, *Eupoecilia ambiguella*, *Euproctis spp.*, *Euxoa spp.*, *Grapholita spp.*, *Hedya nubiferana*, *Hellothis spp.*, *Hellula undalis*, *Hyphantria cunea*, *Keiferia lycopersicella*, *Leucoptera scitella*, *Lithocollethis spp.*, *Lobesia botrana*, *Lymantria spp.*, *Lyonefta spp.*, *Malacosoma spp.*, *Mamestra brassicae*, *Manduca sexta*, *Operophtera spp.*, *Ostrinia nubilalis*, *Pammene spp.*, *Pandemis spp.*, *Panolis flammea*, *Pectinophora gossypiella*, *Phthorimaea operculella*, *Pieris rapae*, *Pieris spp.*, *Plutella xylostella*, *Prays spp.*, *Scirpophaga spp.*, *Sesamia spp.*, *Sparganothis spp.*, *Spodoptera spp.*, *Synanthedon spp.*, *Thaumetopoea spp.*, *Tortrix spp.*, *Trichoplusia ni* and *Yponomeuta spp.*;

insects of the order Coleoptera, for example *Agriotes spp.*, *Anthonomus spp.*, *Atomaria linearis*, *Chaetocnema tibialis*, *Cosmopolites spp.*, *Curculio spp.*, *Dermestes spp.*, *Diabrotica spp.*, *Epilachna spp.*, *Eremnus spp.*, *Leptinotarsa decemlineata*, *Lissorhoptms spp.*, *Melolontha spp.*, *Orycaephilus spp.*, *Otiorhynchus spp.*, *Phlyctinus spp.*, *Popillia spp.*, *Psylliodes spp.*, *Rhizopertha spp.*, *Scarabeidae*, *Sitophilus spp.*, *Sitotroga spp.*, *Tenebrio spp.*, *Tribolium spp.* and *Trogoderma spp.*;

insects of the order Orthoptera, for example *Blatta spp.*, *Blattella spp.*, *Gryllotalpa spp.*, *Leucophaea maderae*, *Locusta spp.*, *Periplaneta spp.* and *Schistocerca spp.*;

insects of the order Isoptera, for example *Reticulitermes spp.*;

insects of the order Psocoptera, for example *Liposcelis spp.*;

insects of the order Anoplura, for example *Haematopinus spp.*, *Linognathus spp.*, *Pediculus spp.*, *Pemphigus spp.* and *Phylloxera spp.*;

insects of the order Mallophaga, for example *Damalinea spp.* and *Trichodectes spp.*;

insects of the order Thysanoptera, for example *Franklin-iella spp., Hercinothrips spp., Taeniothrips spp., Thrips palmi, Thrips tabaci* and *Scirtothrips aurantii;* insects of the order Heteroptera, for example *Cimex spp., Distantiella theobroma, Dysdercus spp., Euchistus spp., Eurygaster spp., Leptocorisa spp., Nezara spp., Piesma spp., Rhodnius spp., Sahlbergella singularis, Scotinophara spp.* and *Triatoma spp.;* insects of the order Homoptera, for example *Aleurothrixus floccosus, Aleyrodes brassicae, Aonidiella spp., Aphididae, Aphis spp., Aspidiotus spp., Bemisia tabaci, Ceroplaster spp., Chrysomphalus aonidium, Chrysomphalus dictyospermi, Coccus hesperidum, Empoasca spp., Eriosoma larigerum, Erythroneura spp., Gascardia spp., Laodelphax spp., Lecanium corni, Lepidosaphes spp., Macrosiphus spp., Myzus spp., Nephotettix spp., Nilaparvata spp., Paratoria spp., Pemphigus spp., Planococcus spp., Pseudaulacaspis spp., Pseudococcus spp., Psylla spp., Pulvinaria aethiopica, Quadraspidiotus spp., Rhopalosiphum spp., Saissetia spp., Scaphoideus spp., Schizaphis spp., Sitobion spp., Trialeurodes vaporariorum, Trioza erytreae* and *Unaspis citri;* insects of the order Hymenoptera, for example Acromyrmex, *Atta spp., Cephus spp., Diprion spp.,* Diprionidae, *Gilpinia polytoma, Hoplocampa spp., Lasius spp., Monomorium pharaonis, Neodiprion spp., Solenopsis spp.* and *Vespa spp.;* insects of the order Diptera, for example *Aedes spp., Antherigona soccata, Bibio hortulanus, Calliphora erythrocephala, Ceratitis spp., Chrysomyia spp., Culex spp., Cuterebra spp., Dacus spp., Drosophila melanogaster, Fannia spp., Gastrophilus spp., Glossina spp., Hypoderma spp., Hyppobosca spp., Liriomyza spp., Lucilia spp., Melanagromyza spp., Musca spp., Oestrus spp., Orseolia spp., Oscinella frit, Pegomyia hyoscyami, Phorbia spp., Rhagoletis pomonella, Sciara spp., Stomoxys spp., Tabanus spp., Tannia spp.* and *Tipula spp.;* insects of the order Siphonaptera, for example *Ceratophyllus spp.* and *Xenopsylla cheopis;* insects of the order Thysanura, for example *Lepisma saccharina;* or

(10) representatives of the order Acarina, for example *Acarus siro, Aceria sheldoni, Aculus schlechtendali, Amblyomma spp., Argas spp., Boophilus spp., Brevipalpus spp., Bryobia praetiosa, Calipitrimerus spp., Chorioptes spp., Dermanyssus gallinae, Eotetranychus carpini, Eriophyes spp., Hyalomma spp., Ixodes spp., Olygonychus pratensis, Ornithodoros spp., Panonychus spp., Phyllocoptruta oleivora, Polyphagotarsonemus latus, Psoroptes spp., Rhipicephalus spp., Rhizoglyphus spp., Sarcoptes spp., Tarsonemus spp.* and *Tetranychus spp.*

The compounds I used according to the invention are preventively and/or curatively valuable active ingredients even at low rates of concentration in the fields of insect control according to (A) and pest control according to (B), while being well tolerated by warmblooded animals, fish, useful insects and plants. The active ingredients used according to the invention are effective against all or individual development stages of normally sensitive and also resistant insects according to (A) and pests according to (B). The activity of the active ingredients used according to the invention may manifest itself directly, that is to say, in the death of the insects according to (A) or the pests according to (B) which occurs immediately or only at a later date, for example at moulting, or indirectly, for example in reduced oviposition and/or a reduced hatching rate, good activity corresponding to a mortality of at least from 50 to 60%. The active ingredients used according to the invention are especially distinguished by the fact that, in particular, useful insects, such as *Amblyseius fallacis, Chrysopa carnea, Coccinella septempunctata, Orius majusculus* and *Typhlodromus pyri,* and birds are not harmed.

With the active ingredients used according to the invention it is especially possible according to (A) to control, that is to say, inhibit or destroy, insects that occur on plants, especially on useful plants and ornamentals, in agriculture, horticulture and in forestry, or on parts of such plants, such as fruit, blossoms, leaves, stems, tubers or roots, while in some cases, at the same time, the parts of plants which grow later are also protected against such insects, and, according to (B), to control, that is to say, inhibit or destroy, pests that occur on plant propagation material, especially on propagation material of useful plants and ornamentals, in agriculture, in horticulture and in forestry, while at the same time the parts of plants which grow later are also protected against such pests, that is to say, for example, the protection lasts until mature resistant plants have developed, the propagation material or the plants developing therefrom being protected both against pests that attack the parts of the plants above the ground and also against pests that live in the soil.

Target crops according to (A) and plant propagation material according to (B) are especially crops and propagation material of cereals, such as wheat, barley, rye, oats, rice maize or sorghum; beet crops, such as sugar beet and fodder beet; fruit, for example pomes, stone fruit and soft fruit, such as apples, pears, plums, peaches, almonds, cherries or berries, for example strawberries, raspberries and blackberries; leguminous plants, such as beans, lentils, peas or soybeans; oil plants, such as rape, mustard, poppy, olives, sunflowers, coconut, castor oil plants, cocoa beans or groundnuts; cucumber plants, such as cucumber, marrows or melons; fibre plants, such as cotton, flax, hemp or jute; citrus fruit, such as oranges, lemons, grapefruit or mandarins; vegetables, such as spinach, lettuce, asparagus, cabbages, carrots, onions, tomatoes, potatoes or paprika; lauraceae, such as avocados, cinnamon or camphor; or tobacco, nuts, coffee, aubergines, sugar cane, tea, pepper, vines, hops, bananas, natural rubber plants or ornamentals, especially of cereals, fruit, leguminous plants, cucumber plants, cotton, citrus fruit, vegetables, aubergines, vines, hops or ornamentals, more especially peaches, beans, peas, marrows, citrus fruit, cabbages, tomatoes, potatoes or aubergines, most especially peaches, marrows, tomatoes or potatoes.

Within the scope of areas (A) and (B) of the subject of the invention, it is possible to control especially a) *Aphis gossypii, Bemisia tabaci* or *Trialeurodes vaporariorum* in tomato crops or tomato propagation material, b) *Aphis gossypii* or *Macrosiphum euphorbiae* in potato crops or potato propagation material, or c) *Aphis gossypii, Bemisia tabaci* or *Trialeurodes vaporariorum* in cucumber crops or cucumber propagation material.

Other fields of application of the active ingredients used according to the invention are: protection of stored goods or stocks or materials or, in the hygiene sector, especially protection of domestic animals or productive livestock against insects according to (A) and pests according to (B).

The invention accordingly relates also to corresponding compositions, that is to say, insecticidal compositions for use according to (A) and pesticidal compositions for use according to (B), such as emulsifiable concentrates, suspension concentrates, directly sprayable or dilutable solutions, coatable pastes, dilute emulsions, wettable powders, soluble powders, dispersible powders, dusts, granules or encapsulations in polymer substances, which compositions comprise—at least—one of the compounds used according to the invention and the type of formulation being chosen in accordance with the intended objectives and the prevailing circumstances, to the use of those insecticidal compositions for application in a method according to (A) and to the use of those pesticidal compositions for application in a method according to (B).

The active ingredient is used in those compositions in pure form, a solid active ingredient, for example, in a specific particle size, or preferably together with—at least—one of the adjuvants customarily employed in formulation technology, such as extenders, for example solvents or solid carriers, or such as surface-active compounds (surfactants).

Suitable solvents are, e.g.: aromatic hydrocarbons or partially hydrogenated aromatic hydrocarbons, preferably the fractions containing 8 to 12 carbon atoms of alkylbenzenes, e.g. xylene mixtures, alkylated naphthalenes or tetrahydronaphthalene, aliphatic or cycloaliphatic hydrocarbons such as paraffins or cyclohexane, alcohols, such as ethanol, propanol or butanol, glycols and their ethers and esters, such as propylene glycol, dipropylene glycol ether, ethylene glycol or ethylene glycol monomethyl or monoethyl ether, ketones, such as cyclohexanone, isophorone or diacetone alcohol, strongly polar solvents, such as N-methylpyrrolid-2-one, dimethyl sulfoxide or N,N-dimethylformamide, water, vegetable oils or epoxidised vegetable oils, such as rape oil, castor oil, coconut oil or soybean oil, or epoxidised rape oil, castor oil, coconut oil or soybean oil, and silicone oils.

The solid carriers used e.g. for dusts and dispersible powders are normally natural mineral fillers such as calcite, talcum, kaolin, montmorillonite or attapulgite. In order to improve the physical properties it is also possible to add highly dispersed silicic acids or highly dispersed absorbent polymers. Suitable granulated adsorptive carders are porous types, for example pumice, broken brick, sepiolite or bentonite; and suitable nonsorbent carriers are, for example, calcite or sand. In addition, a great number of granulated materials of inorganic or organic nature can be used, especially dolomite or pulverised plant residues.

Depending on the nature of the compound to be formulated, suitable surface-active compounds are nonionic, cationic and/or anionic surfactants or surfactant mixtures having good emulsifying, dispersing and wetting properties. The surfactants given below are to be regarded only as examples; many other surfactants that are customarily used in formulation technology and are suitable according to the invention are described in the relevant literature.

Non-ionic surfactants are preferably polyglycol ether derivatives of aliphatic or cycloaliphatic alcohols, saturated or unsaturated fatty acids and alkylphenols, said derivatives containing 3 to 30 glycol ether groups and 8 to 20 carbon atoms in the (aliphatic) hydrocarbon moiety and 6 to 18 carbon atoms in the alkyl moiety of the alkylphenols. Further suitable non-ionic surfactants are the water-soluble adducts of polyethylene oxide with polypropylene glycol, ethylenediaminopolypropylene glycol and alkylpolypropylene glycol containing 1 to 10 carbon atoms in the alkyl chain, which adducts contain 20 to 250 ethylene glycol ether groups and 10 to 100 propylene glycol ether groups. These compounds usually contain 1 to 5 ethylene glycol units per propylene glycol unit. Representative examples of non-ionic surfactants are nonylphenolpolyethoxyethanols, castor oil polyglycol ethers, polypropylene/polyethylene oxide adducts, tributylphenoxy-polyethoxyethanol, polyethylene glycol and octylphenoxy-polyethoxyethanol. Fatty acid esters of polyoxyethylene sorbitan, e.g. polyoxyethylene sorbitan trioleate, are also suitable.

Cationic surfactants are preferably quaternary ammonium salts which contain, as N-substituent, at least one $C_8$–$C_{22}$alkyl radical and, as further substituents, unsubstituted or halogenated lower alkyl, benzyl or hydroxy-lower alkyl radicals. The salts are preferably in the form of halides, methylsulfates or ethylsulfates, e.g. stearyltrimethyl-ammonium chloride or benzyldi(2-chloroethyl) ethylammonium bromide.

Both water-soluble soaps and also water-soluble synthetic surface-active compounds are suitable anionic surfactants. Suitable soaps are the alkali metal salts, alkaline earth metal salts or unsubstituted or substituted ammonium salts of higher fatty acids ($C_{10}$–$C_{22}$), e.g. the sodium or potassium salts of oleic or stearic acid or of natural fatty acid mixtures which can be obtained e.g. from coconut oil or tall oil. Fatty acid methyltaurin salts may also be mentioned as surfactants. More frequently, however, synthetic surfactants are used, especially fatty sulfonates, fatty sulfates, sulfonated benzimidazole derivatives or alkylarylsulfonates. The fatty sulfonates or sulfates are usually in the form of alkali metal salts, alkaline earth metal salts or unsubstituted or substituted ammonium salts and generally contain a $C_8$–$C_{22}$alkyl radical which also includes the alkyl moiety of acyl radicals, e.g. the sodium or calcium salt of lignosulfonic acid, of dodecylsulfate or of a mixture of fatty alcohol sulfates obtained from natural fatty acids. These compounds also comprise the salts of sulfated and sulfonated fatty alcohol/ethylene oxide adducts. The sulfonated benzimidazole derivatives preferably contain 2 sulfonic acid groups and one fatty acid radical containing approximately 8 to 22 carbon atoms. Examples of alkylarylsulfonates are the sodium, calcium or triethanolammonium salts of dodecylbenzenesulfonic acid, dibutylnaphthalenesulfonic acid, or of a condensate of naphthalenesulfonic acid and formaldehyde. Also suitable are corresponding phosphates, e.g. salts of the phosphoric acid ester of an adduct of p-nonylphenol with 4 to 14 moles of ethylene oxide, or phospholipids.

The compositions generally comprise from 0.1 to 99%, especially 0.1 to 95%, of active ingredient and 1 to 99.9%, especially 5 to 99.9%, of—at least—one solid or liquid adjuvant, it generally being possible for 0 to 25%, especially 0.1 to 20%, of the composition to consist of a surfactant (% denotes percentage by weight in each case). Whereas commercial produces will preferably be formulated as concentrates, the end user will normally employ dilute formulations having substantially lower concentrations of active ingredient. Preferred compositions are composed in particular of the following constituents (throughout, percentages are by weight):

Emulsifiable concentrates:
active ingredient: 1 to 90%, preferably 5 to 20%
surfactant: 1 to 30%, preferably 10 to 20%
solvent: 5 to 98%, preferably 70 to 85%
Dusts:
active ingredient: 0.1 to 10%, preferably 0.1 to 1%
solid carrier: 99.9 to 90%, preferably 99.9 to 99%
Suspension concentrates:
active ingredient: 5 to 75%, preferably 10 to 50%
water: 94 to 24%, preferably 88 to 30%
surfactant: 1 to 40%, preferably 2 to 30%
Wettable powders:
active ingredient: 0.5 to 90%, preferably 1 to 80%
surfactant: 0.5 to 20%, preferably 1 to 15%
solid carrier: 5 to 99%, preferably 15 to 98%

Granules:

active ingredient: 0.5 to 30%, preferably 3 to 15% solid carrier: 99.5 to 70%, preferably 97 to 85%

The action of the compositions according to the invention can be substantially broadened and adapted to prevailing circumstances by the addition of other, for example insecticidally, acaricidally and/or fungicidally active, active ingredients. Suitable active ingredient additives are, for example, representatives of the following classes of active substance: organophosphorus compounds, nitrophenols and derivatives thereof, formamidines, ureas, carbamates, pyrethroids, chlorinated hydrocarbons and Bacillus thuringiensis preparations. The compositions according to the invention may also comprise other solid or liquid adjuvants, such as stabilisers, for example vegetable oils or epoxidised vegetable oils (for example epoxidised coconut oil, rape oil or soybean oil), antifoams, for example silicone oil, preservatives, viscosity regulators, binders and/or tackifiers, and also fertilisers or other active ingredients for obtaining special effects, for example bactericides, nematicides, molluscicides or selective herbicides.

The compositions according to the invention are prepared in a manner known per se: in the absence of adjuvants, for example, by grinding and/or sieving, for example to a specific particle size, or by compressing a solid active ingredient, and, in the presence of at least one adjuvant, for example, by intimately mixing and/or grinding the active ingredient with the adjuvant(s). The invention relates also to those processes for the preparation of the compositions according to the invention and to the use of the compounds I in the preparation of those compositions.

Suitable methods of application for the compositions according to (A), that is to say, suitable methods of controlling insects according to (A), are, depending on the intended objectives and the prevailing circumstances, for example, spraying, atomising, dusting, coating, scattering or pouring. Typical rates of concentration are from 0.1 to 1000 ppm, preferably from 0.1 to 500 ppm, of active ingredient. In particular, spray mixtures with active ingredient concentrations of 50, 100, 200, 300 or 500 ppm are used. The rates of application per hectare are generally from 1 to 2000 g of active ingredient per hectare, especially from 10 to 1000 g/ha, preferably from 20 to 600 g/ha. Rates of application of 100, 200, 250, 300, 400 or 450 g of active ingredient per hectare are preferred. Rates of application of 0.25, 0.75, 1.0 or 2.0 g of active ingredient per tree are preferred in the case of application in tree plantations. A preferred method of application for the compositions according to (A) is application to the leaves of the plants (foliar application), the frequency and rate of application depending on the risk of infestation by the particular insect. However, the active ingredient can also penetrate the plant through the roots (systemic action) if the locus of the plant is impregnated with a liquid formulation, or if the active ingredient is incorporated in solid form into the locus of the plant, for example into the soil, for example in granular form (soil application). In paddy rice crops, such granules may be applied in metered amounts to the flooded rice field.

Methods of application for the compositions according to (B), that is to say, methods of protecting plant propagation material, which, according to the invention, is any plant material from which, after planting out or sowing at the site of planting out or sowing, complete plants can develop, for example seedlings, rhizomes, slips, cuttings or, especially, seed, such as fruits, tubers, grains or bulbs, against attack by pests, comprise, for example, applying corresponding compositions in such a manner that their application is effected in close spatial proximity to or spatially together with the planting out or sowing of the propagation material at the site of planting out or sowing. The application of those compositions in close spatial proximity to the planting out or sowing of the propagation material at the site of planting out or sowing is, according to the invention, effected, preferably before planting out or sowing the propagation material, by soil application of the compositions directly at the site of planting out or sowing the propagation material, for example, preferably before sowing, into the seed furrow, or to a narrowly restricted area around the site of planting out or sowing the propagation material, it being possible to carry out that soil application according to (B), for example, in a manner analogous to the soil application according to (A) described above. The application of the corresponding compositions that is effected spatially together with the planting out or sowing of the propagation material at the site of planting out or sowing is to be understood according to the invention as meaning that propagation material pretreated with those compositions is planted out or sown at the site of planting out or sowing, it being possible, depending on the intended objectives and the prevailing circumstances, for the pre-treatment of the propagation material to be effected, for example, by applying the compositions to the propagation material by spraying, atomising, dusting, coating, scattering or pouring, or, in the case of seed, especially also by dressing the seed. In the case of the seed dressing operation according to the invention, that is to say, dry, moist, wet or slurry dressing, a suitable pesticidal composition according to (B) is added to the seed in a dressing apparatus before sowing and the composition is uniformly distributed over the seed, for example, by stirring the contents of the dressing apparatus and/or by rotating and/or shaking the entire dressing apparatus. Special methods of effecting that dressing operation comprise, for example, impregnating the seed with a liquid composition, coating the seed with a solid composition (seed coating) or causing the active ingredient to penetrate into the seed by adding the composition to the water used for pre-soaking the seed (seed soaking). In the case of the seed dressing operation according to the invention, the typical rates of application of the compositions used are, for example, from 0.1 to 20 g of active ingredient per kg of seed, especially from 0.5 to 15 g/kg, preferably from 1 to 10 g/kg, while for the other methods of application according to (B) typical rates of concentration and rates of application are those mentioned above for the methods of application according to (A). The seed dressing according to the invention is distinguished especially by the fact that, owing to the low toxicity of the active ingredient used, good toleration of the dressed seed is observed in birds, for example birds that, as seed-stealers in the wild, tend to take seed from freshly sown fields, such as buntings, blackbirds, thrushes, ducks, pheasants, finches, geese, linnets, chickens, crows, larks, titmice, seagulls, ravens, partridges, ring-doves, goldfinches, pigeons or siskins. The seed dressing according to the invention also comprises the dressing of stored seed.

The invention relates also to the plant propagation material that has been pre-treated according to the invention and that is marketable.

The following Examples serve to illustrate the invention. They do not limit the invention. Temperatures are given in degrees Celsius.

Formulation Examples (throughout, percentages are by weight)

| Example F1: Solutions | a) | b) | c) | d) |
|---|---|---|---|---|
| active ingredient | 80% | 10% | 5% | 95% |
| ethylene glycol monomethyl ether | 20% | — | — | — |
| polyethylene glycol (mol. wt 400) | — | 70% | — | — |
| N-methyl-2-pyrrolidone | — | 20% | — | — |
| epoxidised coconut oil | — | — | 1% | 5% |
| petroleum fraction (boiling range 160–190°) | — | — | 94% | — |

These solutions are suitable for application in the form of micro-drops.

| Example F2: Granules | a) | b) | c) | d) |
|---|---|---|---|---|
| active ingredient | 5% | 10% | 8% | 21% |
| kaolin | 94% | — | 79% | 54% |
| highly dispersed silicic acid | 1% | — | 13% | 7% |
| attapulgite | — | 90% | — | 18% |

The active ingredient is dissolved in dichloromethane, the solution is sprayed onto the carrier, and the solvent is subsequently evaporated off in vacuo.

| Example F3: Dusts | a) | b) |
|---|---|---|
| active ingredient | 2% | 5% |
| highly dispersed silicic acid | 1% | 5% |
| talcum | 97% | — |
| kaolin | — | 90% |

Ready-for-use dusts are obtained by intimately mixing the carriers with the active ingredient.

| Example F4: Wettable powders | |
|---|---|
| active ingredient | 25% |
| sodium sulfate | 5% |
| castor oil polyethylene glycol ether (36–37 mol of ethylene oxide) | 10% |
| silicone oil | 1% |
| Agridex | 2% |
| highly dispersed silicic acid | 10% |
| kaolin powder | 37% |
| sulfite spent lye powder | 5% |
| Ultravon W-300% (disodium salt of 1-benzyl-2-heptadecylbenzimidazole-X,X'-disulfonic acid) | 5% |

The active ingredient is mixed with the adjuvants and the mixture is ground in a suitable mill, affording wettable powders which can be diluted with water to give suspensions of the desired concentration.

| Example F5: Dusts | a) | b) |
|---|---|---|
| active ingredient | 5% | 8% |
| talcum | 95% | — |
| kaolin | — | 92% |

Ready-for-use dusts are obtained by mixing the active ingredient with the carrier and grinding the mixture in a suitable mill.

| Example F6: Extruder granules | |
|---|---|
| active ingredient | 10% |
| sodium lignosulfonate | 2% |
| carboxymethylcellulose | 1% |
| kaolin | 87% |

The active ingredient is mixed and ground with the adjuvants, and the mixture is subsequently moistened with water. The moist mixture is extruded and granulated and then the granules are dried in a stream of air.

| Example F7: Coated granules | |
|---|---|
| active ingredient | 3% |
| polyethylene glycol (mol. wt. 200) | 3% |
| kaolin | 94% |

The finely ground active ingredient is uniformly applied, in a mixer, to the kaolin moistened with polyethylene glycol. Non-dusty coated granules are obtained in this manner.

| Example F8: Suspension concentrate | |
|---|---|
| active ingredient | 40% |
| ethylene glycol | 10% |
| nonylphenol polyethylene glycol ether (15 mol of ethylene oxide) | 6% |
| sodium lignosulfonate | 10% |
| carboxymethylcellulose | 1% |
| aqueous formaldehyde solution (37%) | 0.2% |
| aqueous silicone oil emulsion (75%) | 0.8% |
| water | 32% |

The finely ground active ingredient is intimately mixed with the adjuvants, giving a suspension concentrate from which suspensions of any desired concentration can be obtained by dilution with water.

| Example F9: Emulsifiable concentrates | a) | b) | c) |
|---|---|---|---|
| active ingredient | 25% | 40% | 50% |
| calcium dodecylbenzenesulfonate | 5% | 8% | 6% |
| castor oil polyethylene glycol ether (36 mol of ethylene oxide) | 5% | — | — |
| tributylphenol polyethylene glycol ether (30 mol of ethylene oxide) | — | 12% | 4% |
| cyclohexanone | — | 15% | 20% |
| xylene mixture | 65% | 25% | 20% |

Emulsions of any desired concentration can be produced from such concentrates by dilution with water.

| Example F10: Wettable powders | a) | b) | c) |
|---|---|---|---|
| active ingredient | 25% | 50% | 75% |
| sodium lignosulfonate | 5% | 5% | — |
| sodium laurylsulfate | 3% | — | 5% |
| sodium diisobutylnaphthalene-sulfonate | — | 6% | 10% |
| octylphenol polyethylene glycol ether (7–8 mol of ethylene oxide) | — | 2% | — |
| highly dispersed silicic acid | 5% | 10% | 10% |
| kaolin | 62% | 27% | — |

The active ingredient is mixed with the adjuvants and the mixture is ground in a suitable mill, affording wettable powders which can be diluted with water to give suspensions of the desired concentration.

| Example F11: Emulsifiable concentrate | |
|---|---|
| active ingredient | 10% |
| octylphenol polyethylene glycol ether (4–5 mol of ethylene oxide) | 3% |
| calcium dodecylbenzenesulfonate | 3% |
| castor oil polyglycol ether (36 mol of ethylene oxide) | 4% |
| cyclohexanone | 30% |
| xylene mixture | 50% |

Emulsions of any required concentration can be obtained from this concentrate by dilution with water.

Biological Examples (throughout, percentages are by weight unless otherwise indicated)

Example B1: Action against *Bemisia tabaci*

Dwarf bean plants are placed in gauze cages and populated with adults of *Bemisia tabaci*. After oviposition, all the adults are removed. 10 days later the plants, with the nymphs on them, are sprayed with an aqueous suspension comprising 50 ppm of the test compound. After a further 14 days, the percentage hatching rate of the eggs is evaluated in comparison with untreated control batches.

Compounds of formula I are 100% effective in this test.

Example B2: Action against *Nilaparvata lugens*

Rice plants two weeks old are treated with an aqueous suspension comprising 50 ppm of the test compound. After the spray coating has dried, the plants are populated with nymphs of *Nilaparvata lugens* and then left to stand for 14 days at 28°. Evaluation is then made. The percentage reduction in the subsequent generation (% activity) is determined by comparing the number of freshly hatched nymphs of the subsequent generation on the treated plants with that on untreated plants.

Compounds of formula I are 100% effective in this test.

Example B3: Dressing action against *Nilaparvata lugens*

100 g of rice seeds and a sufficient amount of a formulation of the test compound to give a ratio of 0.1, 1 or 10 g of active ingredient per kg of seeds are introduced into a glass bottle or a plastics container. By rotating and/or shaking the vessel, the test compound is uniformly distributed on the surface of the seeds. The seeds so dressed are sown in flower-pots. After emergence, the young plants are cultivated in a greenhouse for 2 weeks and then they are each populated in Plexiglas cylinders with 20 nymphs (N–3) of *Nilaparvata lugens*. The cylinders are closed with a net. Evaluation is made 5 days after populating the plants. The percentage reduction in the population (% activity) is determined by comparing the number of surviving individuals on the plants grown from the dressed seeds with that on plants grown from seeds that have not been dressed.

Compounds of formula I exhibit good activity in this test.

Example B4: Dressing action against *Aphis fabae*

100 g of bean seeds and a sufficient amount of a formulation of the test compound to give a ratio of 0.1, 1 or 10 g of active ingredient per kg of seeds are introduced into a glass bottle or a plastics container. By rotating and/or shaking the vessel, the test compound is uniformly distributed on the surface of the seeds. The seeds so dressed are sown in flower-pots (3 seeds per pot). The young plants are cultivated in a greenhouse at 25° to 30° until the 2-leaf stage is reached and then populated with *Aphis fabae*. Evaluation is made 6 days after the plants have been populated. The percentage reduction in the population (% activity) is determined by comparing the number of surviving individuals on the plants grown from the dressed seeds with that on plants grown from seeds that have not been dressed.

Compounds of formula I exhibit good activity in this test.

Example B5: Dressing action against *Myzus persicae*

100 g of sugar beet seeds and a sufficient amount of a paste formulation of the test compound, prepared from a wettable powder and a small amount of water, to give a ratio of 0.1, 1 or 10 g of active ingredient per kg of seeds are introduced into a glass bottle or a plastics container. The closed dressing vessel is moved on a rolling support until the paste has been uniformly distributed on the surface of the seeds. The seeds so dressed (coated) are dried and sown in plastics pots containing loess. The seedlings are cultivated in a greenhouse at 24° to 26°, at a relative humidity of 50 to 60% and with a period of illumination of 14 hours per day. 4 weeks after germination, the plants, which are 10 cm tall, are populated with a mixed population of *Myzus persicae*. Evaluation is made 2 and 7 days after the plants have been populated. The percentage reduction in the population (% activity) is determined by comparing the number of surviving individuals on the plants grown from the dressed seeds with that on plants grown from seeds that have not been dressed.

Compounds of formula I exhibit good activity in this test.

What is claimed is:

1. A method of controlling insects, which comprises applying an insecticidally effective amount of an insecticidal composition, said composition including at least one compound of the formula

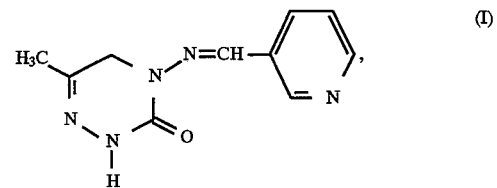

in free form or in agrochemically acceptable salt form, as active ingredient, and at least one adjuvant, to insects of the family Aleyrodidae, Cicadellidae or Delphacidae.

2. A method according to claim 1, wherein the active ingredient is used in free form.

3. A method according to claim 1 of controlling insects of the Aleyrodidae family.

4. A method according to claim 3 of controlling insects of the genus Bemisia or Trialeurodes.

5. A method according to claim 4 of controlling insects of the species *Bemisia tabaci*.

6. A method according to claim 4 of controlling insects of the species *Trialeurodes vaporariorum*.

7. A method according to claim 1 of controlling insects of the Cicadellidae family.

8. A method according to claim 7 of controlling insects of the genus Empoasca or Erythroneura.

9. A method according to claim 1 of controlling insects of the Delphacidae family.

10. A method according to claim 9 of controlling insects of the genus Laodelphax or Nilaparvata.

* * * * *